United States Patent [19]

Entwistle

[11] Patent Number: 4,505,159
[45] Date of Patent: Mar. 19, 1985

[54] TESTING OF WIRE PRIOR TO PLATING

[75] Inventor: Stanley D. Entwistle, Ottawa, Canada

[73] Assignee: Northern Telecom Limited, Montreal, Canada

[21] Appl. No.: 474,443

[22] Filed: Mar. 11, 1983

[51] Int. Cl.³ .................................... G01N 19/08
[52] U.S. Cl. ............................. 73/847; 73/104; 73/432 R
[58] Field of Search ............. 73/104, 847, 799, 432 Z, 73/432 R, 158

[56] References Cited

U.S. PATENT DOCUMENTS

| 2,186,014 | 1/1940 | Ellis | 73/104 |
| 2,236,373 | 3/1941 | Kowalski | 73/104 X |
| 2,735,304 | 2/1956 | Berwick, Jr. | 73/432 Z |
| 2,984,101 | 5/1961 | Minor et al. | 73/104 |

FOREIGN PATENT DOCUMENTS

| 1115456 | 1/1956 | France | 73/847 |
| 121129 | 9/1980 | Japan | 73/847 |
| 12547 | 2/1981 | Japan | 73/104 |
| 237424 | 8/1945 | Switzerland | 73/847 |
| 709101 | 5/1954 | United Kingdom | 73/104 |

Primary Examiner—James J. Gill
Assistant Examiner—Tom Noland
Attorney, Agent, or Firm—Sidney T. Jelly

[57] ABSTRACT

In the plating of wire, particularly gold plating of wire for terminal pins, obtaining a high quality fixed gold plate is a problem. The invention provides for testing the wire prior to plating to detect surface irregularities which affect the quality of the plate. A test length of wire has a length of tape wrapped spirally around, with at least an edge portion in contact with the wire. The wire, and tape, is then twisted, in the direction of the spiral of the tape, in a direction to tighten the tape. The tape is then unwound and the number of particles of wire material which have separated from the wire at defects adhere to the tape is counted. For premium grade wire, less than 6 defects per foot is a standard. Commercial grade wire, between 50 and 150 defects per foot is normal.

5 Claims, 4 Drawing Figures

TESTING OF WIRE PRIOR TO PLATING

This invention relates to the testing of wire prior to plating, and is particularly related to the testing to determine the grade.

Wire terminal pins are usually plated, the stock material being for example, phosphor bronze. The pins are usually gold plated, at least in the area or areas of contact. If locally gold plated then the rest of the terminal pin is usually plated with a less costly material, for example tin, for protection and solderability if necessary.

There are usually underplatings beneath the gold. As an example, the pins may first be copper plated, then nickel plated, a gold strike, then soft gold plated and finally hard gold plated. These steps may vary and again as an example, the gold strike and soft gold plating may be replaced by palladium plating. It is conceivable that, with palladium plating, the final hard gold plating may be omitted, or the hard gold layer much reduced in thickness.

It is a big problem in plating terminal pins to obtain a high quality final gold plate. Surface roughness and porosity are very difficult to control. Presence of these features causes poor quality contact and spalling or erosion of the gold layer on insertion and removal of pins from female terminals.

It has been found that the poor quality of the gold plating is caused by surface irregularities of the base or stock material. Such irregularities can be: inverse segregated phases, surface and sub-surface internal oxidation, entrapped organic contaminants, laps, seams, and burrs. By using premium grade wire the number of irregularities or precursors is considerably reduced. However testing of the wire to determine such number of irregularities is difficult.

Various tests exist, such as visual inspection under a microscope; bend tests followed by visual inspection, the wire having been bent through 80° in a very small radius, or spiral wound on a mandrel. However it has been determined that these tests do not provide an accurate indication of the irregularities.

The present invention tests the wire in such a manner that the irregularities result in small particles of stock material to break away from the wire. By suitable means these are counted.

In accordance with the invention, a short test length of material has a length of tape wrapped spirally around it, with an edge portion of the tape in contact with the wire. The wire is then twisted, the direction of twist that will tighten the tape on the wire. After twisting, the tape is unwound and the edge portion scanned or inspected under a microscope, and the number of particles counted. The test is repeated for further samples, and the results related to a particular length, for example a linear foot of wire. As an indication of results, for premium grade wire, less than 6 defects per foot is a standard, with often 1 defect per foot occurring. With commercial grade wire, between 50 and 150 defects per foot is normal.

The invention is particularly effective for phosphor-bronze wire, and especially of square cross-section, for example 0.025" square. While the invention will be described with such wire, it will be appreciated that the invention is equally applicable to other wire materials and cross-sections.

The invention will be readily understood by the following description in conjunction with the accompanying drawings, which illustrate one particular form of test apparatus, as an example, and in which.

Figure 1:
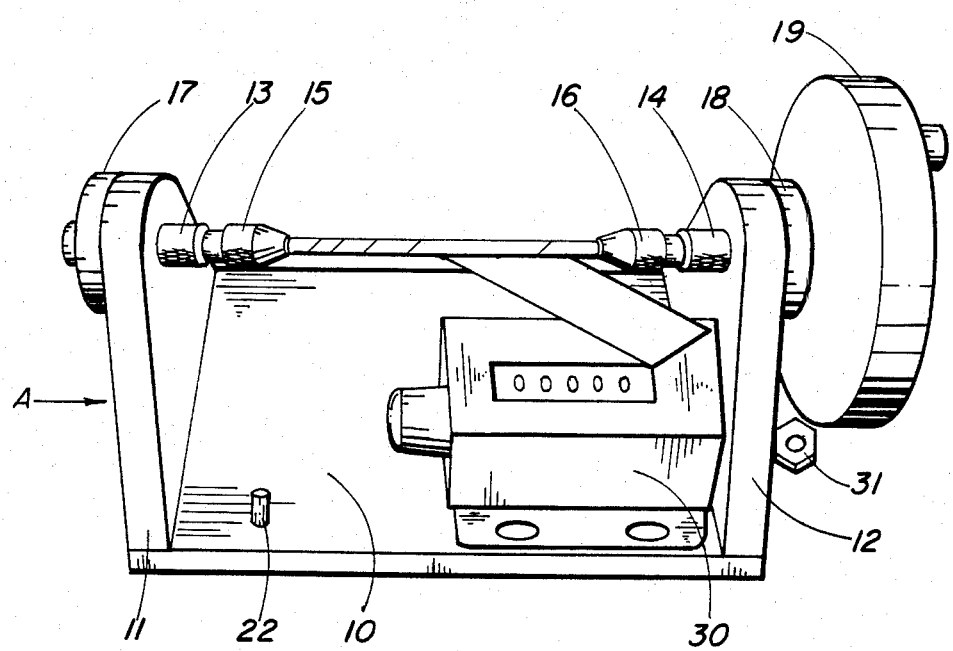
FIG. 1 is a perspective view of the particular form of test apparatus.
Figure 2:
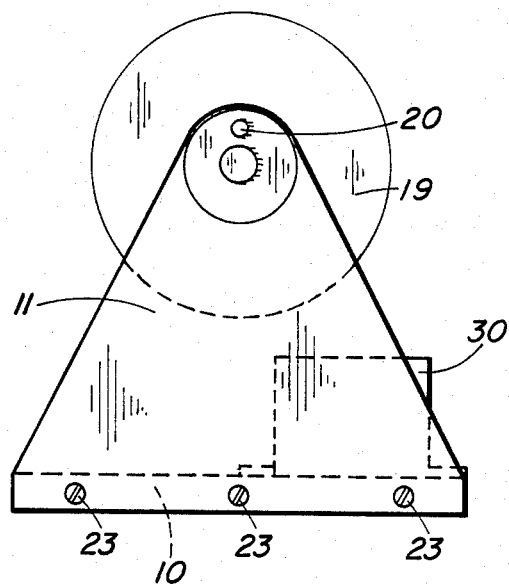
FIG. 2 is an end view of the apparatus in FIG. 1, in the direction of arrow A.
Figure 3:
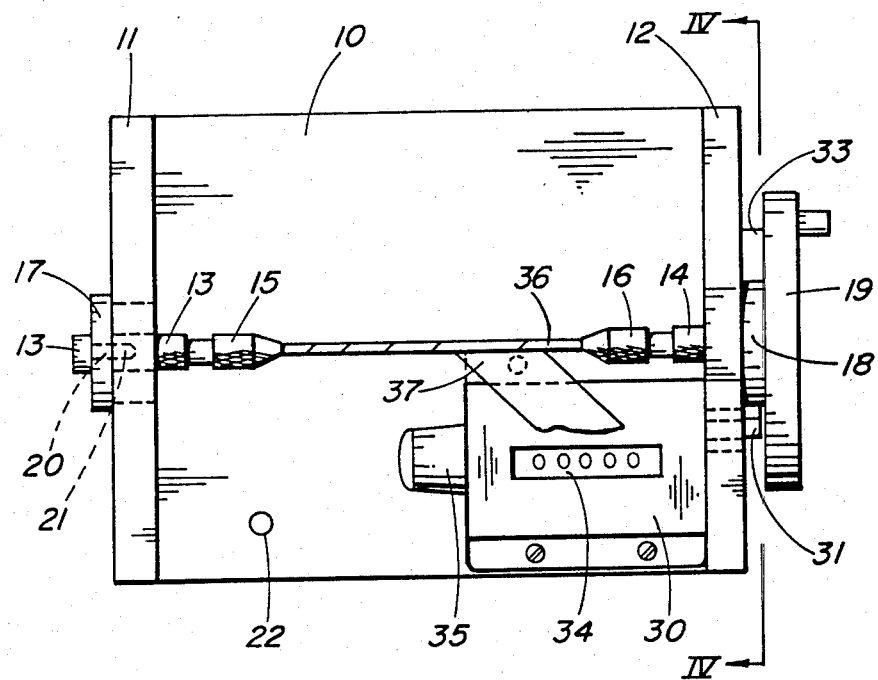
FIG. 3 is a top plan view of the apparatus of FIG. 1.

As illustrated in FIG. 1 particularly, the test apparatus comprises a base 10 with upstanding end walls 11 and 12. In each end wall is rotatably mounted a shaft 13, 14, each shaft carrying a chuck 15 and 16. For square wire the chucks have four jaws. A collar 17 is attached to the outer end of shaft 13 and shaft 14 has a cam member 18 and a disc or handle 19 attached thereto. As readily seen in FIGS. 2 and 3, a small bore 20 extends through the collar 17 and can be aligned with a corresponding bore 21 in the end wall 11. A pin 22, conveniently stored in a bore in the base 10, can be inserted through the bore 20 and also entering bore 21, to prevent collar 17, shaft 13 and chuck 15 from rotating. The end walls 11 and 12 are conveniently attached to the base by screws 23.

Figure 4:
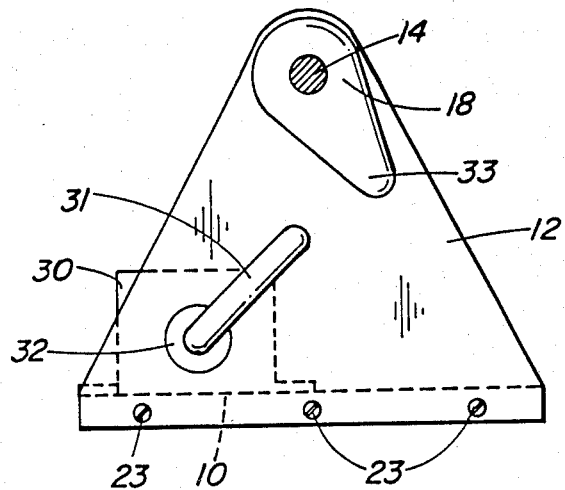
FIG. 4 is a cross-section on the line IV—IV of FIG. 3.

Mounted on the base 10 is a counter 30. The counter has an actuating arm 31 which extends through an aperture 32 in the end wall 12. This is seen in FIG. 4. The cam member 18 has a lobe or extension 33 which engages the arm 31 as the disc or handle 19 is rotated. The indices of the counter 30 are viewed through a window 34 and a reset knob 35 is provided.

In use, a short length of wire is positioned in the chucks 15 and 16, which are then tightened. The collar 17, and shaft 13 are left free to rotate, and a length of tape is wrapped spirally around the wire. The wire is indicated at 36 in FIG. 3 and the partially wrapped tape at 37. The tape is wrapped so as to leave about 1/16" to ⅛" of one edge continuously in contact with the wire, the rest of the tape width overlapping previous turns, except at the beginning. The counter is set to zero and the pin 22 inserted into bores 20 and 21 to hold shaft 13 and chuck 15 against rotation.

The tape is wrapped in a predetermined direction, for example by rotating the wire in a counter-clockwise direction. After locking the collar 17, the handle 19 is rotated in the same direction, that is counter-clockwise, for a predetermined number of turns, twisting the wire 36. After twisting the desired number of turns, the collar 17 is released by removal of the pin 22 and the tape 37 slowly and carefully removed by rotating the wire, via handle 19, in a clockwise direction.

The edge portion of the tape which had been in contact with the wire is then inspected under a microscope, at, as an example, 10 or 20 magnifications, to determine how many particles are attached thereto, the particles detaching at defects.

In the apparatus illustrated about a two inch length of wire is twisted. The samples are obtained as desired. One typical procedure is to remove about five feet from the end of a coil of wire and cut about six test pieces approximately three inches long at random positions in the length.

The tape is of a material which will adhere to a limited extent to the wire and retain displaced particles thereon, and be easily removable. Two examples are Teflon and nylon tape. The particular wire relating to the above described test is phosphor bronze, 0.025" square. The number of turns applied is six. The twisting of the wire in the same direction as when the tape is applied tightens the tape on the wire. If the tape is applied with a clockwise rotation, then the wire is twisted in a clockwise direction. The test results can be averaged for the test pieces, or the test pieces can be considered individually.

The apparatus can be used for wires of other compositions, of other sizes and cross-sections. The size of the apparatus can also be varied to suit. The number of rotations, or twists, applied to the wire, is such as to create substantial stresses at the surface but insufficient to break the wire. The stresses at the surface cause imperfections to lift and break from the surface and adhere to the tape. One typical example of wire is:

tin—4.2–5.8
phosphorus—0.03–0.35
iron max.—0.10
lead max.—0.05
zinc max.—0.30
copper+tin+phosphorus min. 99.5 percent, by wt.

By the use of premium grade wire, carefully tested and checked, the quality of the final plated surface is considerably increased. The quality of gold plating has been increased by a factor of 2 or 3.

What is claimed is:

1. A method of testing wire prior to plating, comprising;
    wrapping a length of tape spirally around a length of wire, at least an edge portion thereof in contact with the wire;
    twisting the wire, and the tape, a number of times, in a direction to tighten the tape;
    unwinding the tape;
    inspecting said continuous edge portion of the tape and counting the number of particles of wire material which are attached to the tape, said particles having been removed from the wire.

2. A method as claimed in claim 1, the twisting of the wire carried out to an amount which creates substantial stresses at the surface of the wire to cause imperfections to lift and break from the surface, the stresses being insufficient to break the wire.

3. A method as claimed in claim 1, the wire being of square cross-section.

4. A method as claimed in claim 1, for testing a copper wire.

5. A method of testing wire for terminal pins prior to gold plating, the wire being of copper based material, the method comprising;
    cutting a length of wire from a coil of wire and cutting a number of test pieces at random positions in said length;
    wrapping a length of tape spirally around each test piece, at least an edge portion thereof in contact with the wire;
    twisting each of said pieces, with the tape, a number of times in a direction to tighten the tape;
    unwinding the tape off each test piece;
    inspecting the test pieces and counting the number of particles of wire material attached to each length of tape;
    relating the number of particles to a predetermined data length.

* * * * *